US005578647A

United States Patent [19]
Li et al.

[11] Patent Number: 5,578,647
[45] Date of Patent: Nov. 26, 1996

[54] METHOD OF PRODUCING OFF-GAS HAVING A SELECTED RATIO OF CARBON MONOXIDE TO HYDROGEN

[75] Inventors: Lixiong Li; Earnest F. Gloyna, both of Austin, Tex.

[73] Assignee: Board of Regents, The University of Texas System, Austin, Tex.

[21] Appl. No.: 359,467

[22] Filed: Dec. 20, 1994

[51] Int. Cl.⁶ .......................... C07C 27/00; C07C 27/10
[52] U.S. Cl. ........................................... 518/700; 518/703
[58] Field of Search ..................................... 518/700, 703

[56] References Cited

U.S. PATENT DOCUMENTS

| | | | |
|---|---|---|---|
| 3,716,474 | 2/1973 | Hess et al. | 208/59 |
| 3,948,754 | 4/1976 | McCollum et al. | 208/11 LE |
| 3,984,311 | 10/1976 | Diesen et al. | 210/63 R |
| 4,141,829 | 2/1979 | Thiel et al. | 210/63 |
| 4,212,735 | 7/1980 | Miller | 252/434 |
| 4,251,227 | 2/1981 | Othmer | 48/197 |
| 4,327,239 | 4/1982 | Dorrance | 585/733 |
| 4,465,888 | 8/1984 | Paspek, Jr. | 585/520 |
| 4,473,459 | 9/1984 | Bose et al. | 208/8 LE |
| 4,483,761 | 11/1984 | Paspek, Jr. | 206/106 |
| 4,543,190 | 9/1985 | Modell | 210/721 |
| 4,559,127 | 12/1985 | Paspek, Jr. | 208/8 LE |
| 4,594,141 | 6/1989 | Paspek, Jr. et al. | 208/390 |
| 4,792,408 | 12/1986 | Titmas | 210/747 |
| 4,818,370 | 4/1989 | Gregoli et al. | 208/106 |
| 4,840,725 | 6/1989 | Paspek | 208/130 |
| 4,861,497 | 8/1989 | Welch et al. | 210/759 |
| 4,898,107 | 2/1990 | Dickinson | 110/346 |
| 5,057,220 | 10/1991 | Harada et al. | 210/605 |
| 5,100,560 | 3/1992 | Huang | 210/721 |
| 5,133,877 | 7/1992 | Rofer et al. | 210/761 |
| 5,200,093 | 4/1993 | Barner et al. | 210/761 |
| 5,232,604 | 8/1993 | Swallow et al. | 210/759 |

FOREIGN PATENT DOCUMENTS

| | | |
|---|---|---|
| 85597/82 | 1/1983 | Australia. |
| 8204075 | 5/1983 | Brazil. |
| 568882 | 11/1993 | European Pat. Off.. |
| 53-91093 | 8/1978 | Japan. |
| 5031000 | 9/1991 | Japan. |
| WO93/22490 | 11/1993 | WIPO. |

OTHER PUBLICATIONS

Baker et al., "Catalytic Destruction of Hazardous Organics in Aqueous Wastes: Continuous Reactor System Experiments," *Hazardous Waste & Hazardous Materials*, 6(1):87–94, 1989.

Crain et al., "Kinetics and Reaction Pathways of Pyridine Oxidation in Supercritical Water," *Ind. Eng. Chem. Res.*, 32(10):2259–2268, 1993.

Huppert et al., "Hydrolysis in Supercritical Water: Identification and Implications of a Polar Transition State," *Ind. Eng. Chem. Res.*, 28:161–165, 1989.

Klein et al., "Hydrolysis in Supercritical Water: Solvent Effects as a Probe of the Reaction Mechanism," *J Supercritical Fluids*, 3:222–227, 1990.

(List continued on next page.)

*Primary Examiner*—Gary Geist
*Attorney, Agent, or Firm*—Arnold, White & Durkee

[57] ABSTRACT

A method of producing an off-gas with a selected $CO/H_2$ ratio of from about 0.1 to about 8 and a $CO/CO_2$ ratio of at least about 0.1 by hydrothermal processing is provided. The method comprises the step of contacting a reactant capable of producing CO and $H_2$ under hydrothermal conditions at a temperature of at least about 374° C. and a pressure of at least about 22.1 MPa in the presence of water and with an amount of an additive effective to produce the selected $CO/H_2$ ratio. The contacting is for a time sufficient to produce off-gas having the selected $CO/H_2$ ratio and having a $CO/CO_2$ ratio of at least about 0.1. Presence of the additive may enhance or may reduce the ratio of carbon monoxide to hydrogen in the off-gas. The additive may be an acid, a base, a salt, an oxide, or an oxidant. The off-gas having a selected $CO/H_2$ ratio may be used for synthesis of organic compounds.

49 Claims, 4 Drawing Sheets

OTHER PUBLICATIONS

McBrayer et al., "Research and Development of a Commercial Supercritical Water Oxidation Process," *Proceedings of the Eleventh Annual Environmental Management and Technology Conference/International*, Atlantic City, NJ, Jun. 9–11, 1993.

McKendry et al., "The Effective of Additives on the Oxidation of Dimethyl Methylphosphonate in Supercritical Water," *Abstract*, Industrial Waste Conference, Purdue University, West Lafayette, Indiana, May 9–11, 1994.

Tester et al., "Supercritical Water Oxidation Technology: A Review of Process Development and Fundamental Research" *ACS Symposium Series Paper.*, Oct. 1–3, Atlanta, Georgia, 1993.

Townsend et al., "Solvent Effects during Reactions in Supercritical Water", *Ind. Eng. Chem. Res.*, 27:143–149, 1988.

Baillod et al., "Fate of Specific Pollutants During Wet Oxidation and Ozonation," *Environ. Prog.*, 1(3), 217–227, 1982.

Day et al., "Oxidation of Propionic Acid Solutions," *Can. J. Chem. Eng.* 51, 733–740, 1973.

Conditt and Sievers, "Microanalysis of Reaction Products in Sealed Tube Wet Air Oxidations by Capillary Gas Chromatography," *Anal. Chem.*, 56:2620–2622, 1984.

Corcoran, "Pyrolysis of n–Butane," *Pyrolysis: Theory and Industrial Practice*, 47–69, 1983.

United States Environmental Protection Agency, "Gas–Phase Chemical Reduction," *Demonstration Bulletin*, EPA/540/MR–93/522, 1993.

Fisher, "Oxidation of Sewage With Air at Elevated Temperatures," *Water Research*, 5:187–201, 1971.

Hurwitz et al., "Wet Air Oxidation of Sewage Sludge," *Water & Sewage Works*, 112(8):298–305, 1965.

Irick, "Manufacture via Hydrocarbon Oxidation," In Acetic Acid and its Derivatives, Ed. by Agreda and Zoeller, Marcel Dekker, Inc., New York, 1993.

Keen and Baillod, "Toxicity to Daphnia of the End Products of Wet Oxidation of Phenol and Substituted Phenols," *Water Res.*, 19(6):767–772, 1985.

McConnell and Head, "Pyrolysis of Ethane and Propane," *Pyrolysis: Theory and Industrial Practice*, Ch. 2, 25–47, 1983.

McGinnis et al., "Conversion of Biomass into Chemicals with High–Temperature Wet Oxidation," *Ind. Eng. Chem. Prod. Res.*, 22(4):633–636, 1983.

Partin and Heise, "Bioderived Acetic Acid," Ch. 1, 3–15, 1993.

Taylor and Weygandt, "A Kinetic Study of High Pressure Aqueous Oxidations of Organic Compounds Using Elemental Oxygen," *Can. J. Chem.*, 52:1925–1933, 1974.

Teletzke et al., "Components of Sludge and Its Wet Air Oxidation Products," *Journal WPCF*, 39(6):994–1005, 1967.

Turner, "Supercritical Water Oxidation of Dimethyl Methylphosphonate and Thiodiglycol," *Ph.D. Dissertation*, Civil Engineering Department, The University of Texas at Austin, Austin, Texas, 1994.

Webley et al., "Oxidation Kinetics of Ammonia and Ammonia–Methanol Mixtures in Supercrital Water in the Temperature Range 530–700 C. at 246 bar," *Ind. Eng. Chem. Res.*, 30:1745–1754, 1991.

"ECO Waste Technologies and the Huntsman Corporation Host an Introduction to SCWO Technology and a Tour of Their SWCO Facilities," *Separations Update*, p. 3, Center for Energy Studies, University of Texas at Austin, Tischler, C., ed., Summer 1994.

Ladendorf, K., "Company hopes treatment cuts waste," *Austin American–Statesman*, pp. D1–D3, Aug. 25, 1994.

LeBlanc et al., "Production of Methanol," *Methanol Production and Use*, pp. 73–113, Ch. 3.3, Chen et al., eds., Marcel Dekker, Inc., New York, 1994.

Zoeller, J. R., "Manufacture via Methanol Carbonylation," *Acetic Acid and its Derivatives*, pp. 35–51, Agreda et al., eds., Marcel Dekker, Inc., New York, 1993.

Gustafson and Zoeller, "Other Synthesis Gas–Based Acetic Acid Processes," *Acetic Acid and its Derivatives*, pp. 53–60, Agreda et al., eds., Marcel Dekker, Inc., New York, 1993.

Herman, R. G., ed., *Catalytic Conversation of Synthesis Gas and Alcohols to Chemicals*, pp. 37–283, Plenum Press, New York, 1984.

METHOD OF PRODUCING OFF-GAS HAVING A SELECTED RATIO OF CARBON MONOXIDE TO HYDROGEN

FIELD OF THE INVENTION

This invention generally relates to a process in which organic materials are converted hydrothermally to produce useful gaseous mixtures in the presence of an additive under supercritical conditions for water. In particular, the ratio of carbon monoxide to hydrogen in the off-gas is controllable in the present process. The off-gas may be used as a source of fuel or raw materials for chemical synthesis.

BACKGROUND OF THE INVENTION

Supercritical water oxidation (SCWO) has been demonstrated to be effective in the destruction of hazardous and toxic wastes. This chemical oxidation process takes place at temperatures above 374.15° C. and 22.1 MPa. Supercritical water acts as a dense gas, with the solvation characteristics of a nonpolar organic solvent; organic material and gases are miscible with supercritical water, yet inorganic salts are virtually insoluble. High destruction efficiencies (>99.99%) over relatively short residence times (on the order of seconds to minutes) are achieved due to the high solubility of organic compounds and oxygen, alleviating mass transfer hindrances. Typically, at supercritical conditions, complete conversion results in carbon dioxide, water, and mineral acids. However, under moderate SWCO conditions, (such as, lower temperatures, shorter residence times and limited amounts of oxidant), some refractory intermediates (e.g., acetic acid, ammonia, or carbon monoxide) have been observed in the reactor effluent. These and other possible reaction intermediates may be useful in themselves or as raw materials in chemical synthesis.

For example, carbon monoxide (CO) and hydrogen ($H_2$) are of commercial interest to the production of synthesis gas (syn gas), a starting material for various chemical syntheses. Three methods are used industrially for generating syn gas: steam reforming of methane; partial oxidation of heavy fuel oil; and coal gasification; for these methods, once a procedure is chosen, the ratio of CO to $H_2$ obtained in the off-gas is typically fixed at a $CO/H_2$ molar ratio of 1/3, 1/1, and 2/1, respectively. Conventionally, the ratio of $CO/H_2$ may be altered via the water gas shift reaction (also called CO conversion reaction):

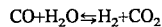

$$CO + H_2O \rightleftharpoons H_2 + CO_2$$

This reaction may be used to shift the $H_2/CO$ ratio in synthesis gas or to alter $H_2$ production.

U.S. Pat. No. 4,251,227 relates to a method for producing substitute natural gas or syn gas from wet solid wastes and low grade fuels under subcritical conditions. U.S. Pat. No. 5,250,193 relates to wet oxidation for destruction of organic components in a wastewater stream contaminated with inorganic salts. U.S. Pat. No. 3,716,474 relates to high pressure thermal treatment of waste oil-containing sludges. U.S. Pat. No. 4,465,888 relates to oligomerization of olefins in supercritical water. U.S. Pat. Nos. 4,594,141 and 4,840,725 relate to the conversion of high boiling organic materials to low boiling materials. U.S. Pat. No. 5,133,877 relates to conversion of hazardous materials using supercritical water oxidation. U.S. Pat. No. 4,483,761 relates to upgrading heavy hydrocarbons with supercritical water and light olefins, and U.S. Pat. No. 5,232,604 relates to a process for the oxidation of materials in water at supercritical temperatures utilizing reaction rate enhancers.

Japanese Patent JP 5031000 relates to a method comprising selectively hydrolysing and/or pyrolysing natural or synthetic high molecular compounds using water under supercritical or subcritical conditions as solvent. Brazilian Patent BR 8204075 and Australian Patent application 8285597 relate to the production of synthesis gas carried out by pretreatment of feedstock under subcritical wet oxidation conditions to convert organic materials to carbon dioxide that is then fed to an existing syn gas producer, either a steam reformer or a partial oxidation gasifier. The reported improvement relates to reducing and controlling the $H_2/CO$ ratio in the synthesis gas by wet oxidizing combustible materials to obtain a gas comprising a mixture of water vapor and carbon dioxide.

Holgate et al. relates to the determination of new kinetic parameters for the water-gas shift reaction and for the direct oxidation of carbon monoxide in supercritical water.

The prior art methods of producing syn gas each have the disadvantage of lacking any control in achieving a particular ratio of $CO/H_2$. A further disadvantage of prior art methods is the loss of carbon as $CO_2$ due to the water gas shift reaction.

SUMMARY OF THE INVENTION

The present invention provides a method of producing an off-gas with a selected $CO/H_2$ ratio of from about 0.1 to about 8 and a $CO/CO_2$ ratio of at least about 0.1 by hydrothermal processing. The method comprises the step of contacting a reactant capable of producing CO and $H_2$ under hydrothermal conditions at a temperature of at least about 374° C. and a pressure of at least about 22.1 MPa in the presence of water and with an amount of an additive effective to produce the selected $CO/H_2$ ratio. The contacting is for a time sufficient to produce off-gas having the selected $CO/H_2$ ratio and having a $CO/CO_2$ ratio of at least about 0.1. Presence of the additive may enhance or may reduce the ratio of carbon monoxide to hydrogen in the off-gas. This method may further comprise the step of preheating the reactant before the contacting step.

A further embodiment of the above-described method comprises the steps of: i) allowing the reactant to react in the presence of water at least at about 22.1 MPa and at a temperature of at least about 374° C. to produce a product; and ii) contacting the product with an amount of an additive effective to produce the selected $CO/H_2$ ratio, said contacting being for a time sufficient to produce off-gas having the selected $CO/H_2$ ratio and having a $CO/CO_2$ ratio of at least about 0.1.

An even further embodiment of the above-described method comprises the steps of: i) contacting the reactant at a temperature of between about 300° C. and 374° C. and a pressure of at least about 22.1 MPa in the presence of water and with an amount of an additive effective to produce the selected $CO/H_2$ ratio, said contacting being for a time sufficient to produce off-gas having the selected $CO/H_2$ ratio; and ii) heating the mixture to at least about 374° C. to remove carbon dioxide as a carbonate salt to produce off-gas having a $CO/CO_2$ ratio of at least about 0.1.

Reactants capable of producing carbon monoxide and hydrogen under hydrothermal conditions may include hydrocarbons; oxygenated hydrocarbons; organic wastes from various industrial processes; lignocellulosic materials, such as wood, paper, or vegetation; sewage sludge;

industrial sludge or fossil fuels such as coal or petrochemicals.

A preferred embodiment of the methods of the present invention is where the additive increases the ratio of carbon monoxide to hydrogen in the off-gas to a value from 0.1 to about 8.0, preferably from 0.2 to 4.0, more preferably from 0.3 to 2.0 and most preferably from 0.3 to 1.5. A preferred temperature range is between about 400° C. and 500° C.

The additive may be an acid, a base, a salt, or an oxide. The additive may be an oxidant except in the method where the initial heating step is at subcritical temperatures. When the additive is an acid, the acid is selected from the group consisting of boric, carbonic, hydrogen halide, nitric, phosphoric, and sulfuric acid. Hydrogen halide acids may be HCl, HBr, HI or HF. Other oxidation states of these acids are contemplated in the invention, such as, for example, nitrous acid, sulfurous acid and perchloric acid. A preferred acid is phosphoric acid.

The additive may be a base, and the base may be a hydroxide form of a group IA metal, group IIA metal, or a transition metal. Group IA metals include, for example, Li, Na, K, Rb, and Cs. Group IIA metals include, for example, Be, Mg, Ca, Sr, and Ba. Transition metals include, for example, Mn, Cu, and Zn. A preferred base is NaOH. The additive may be a salt and the salt may be formed from a reaction between a metal herein-described and an acid herein-described. The additive may be an oxide, and the oxide may be an oxide of a group IIIA element (for example, B, Al, Ga, In, or Tl), a group IVA element (for example, C, Si, Ge, Sn, or Pb), or a peroxide. The oxidant may be oxygen or hydrogen peroxide.

A preferred embodiment of the invention comprises the further step of controlling the time of the reacting: preferably, the time is between about 5 and 300 seconds, or more preferably, between about 5 and 100 seconds, or most preferably the time is between about 7 and 14 seconds.

The additive may be added in an amount less than or equal to the solubility of the additive during the contacting step. The additive may also be added in amounts sufficient to precipitate $CO_2$ and this process is for in situ separation. U.S. Pat. No. 4,822,497 and U.S. Ser. No. 08/142,777, both incorporated by reference herein, describe an apparatus usable for solid separation.

In a preferred embodiment, the additive may be added in a molar ratio to reactant carbon of between about 0.001 and 0.1, or may be added in a ratio of 1. For sludge, garbage or wastewater, a total organic carbon analysis is performed using an instrument called a Total Organic Carbon Analyzer known to one of skill in this art.

In a further preferred embodiment, the off-gas having the selected $CO/H_2$ ratio is obtained. The off-gas so obtained may be for synthesis of further organic compounds, such as, for example, paraffins, alkanes such as methane, olefins such as ethylene, alcohols such as methanol, diols such as ethylene glycol, monocarboxylic acids such as acetic acid, esters such as ethyl acetate or vinyl acetate, or polymers.

The off-gas has preferred "ratio" of carbon monoxide to hydrogen of: about 0.33 for the synthesis of alkanes; of about 0.5 for the synthesis of alkenes; of between about 0.5 and 0.66 for the synthesis of alcohols; and of between about 0.66 and 1.0 for the synthesis of carboxylic acids or esters.

A further aspect of the present invention is the use of the syn gas made by the present inventive method in the synthesis of chemicals. A method of making an alkane is an aspect of the present invention and comprises the following steps: i) contacting a reactant capable of producing CO and $H_2$ under hydrothermal conditions at a temperature of at least about 374° C. and a pressure of at least about 22.1 MPa in the presence of water and with an amount of an additive effective to produce a $CO_2/H_2$ ratio of about 0.33, said contacting being for a time sufficient to produce off-gas having a $CO/H_2$ ratio of about 0.33 and having a $CO/CO_2$ ratio of at least about 0.1; and ii) reacting the off-gas in the presence of a catalyst and at a temperature and a pressure that optimally produces the alkane. Preferred alkanes are lower alkanes such as methane, ethane, propane or butane, or isomers thereof. A more preferred alkane is methane. Traditionally, a preferred catalyst is cerium-nickel or a zeolite. The catalyst may be a metal selected from the group consisting of Y, La, Pr, Th, Nd, Sm, Eu, U, Ca, Zr, and Hf.

A further preferred embodiment of the present invention is a method of producing an alcohol comprising the steps of: i) contacting a reactant capable of producing CO and $H_2$ under hydrothermal conditions at a temperature of at least about 374° C. and a pressure of at least about 22.1 MPa in the presence of water and with an amount of an additive effective to produce a $CO/H_2$ ratio of between about 0.5 and 0.66, said contacting being for a time sufficient to produce off-gas having a $CO/H_2$ ratio of between about 0.5 and 0.66 and having a $CO/CO_2$ ratio of at least about 0.1; and ii) reacting the off-gas in the presence of a catalyst and at a temperature and a pressure that optimally produces the alcohol. Preferred alcohols are methanol, ethanol, propanol, or butanol, or isomers thereof. A more preferred alcohol is methanol. Traditionally, a preferred catalyst is thorium-copper, $Cu/ZnO/Cr_2O_3$ or $Cu/ZnO/Al_2O_3$. One skilled in the art, in light of the present disclosure, is able to optimize the conditions of time, temperature and pressure for production of methanol. Methanol is itself a precursor to several further commonly used organic compounds, such as, formaldehyde or acetic acid, for example.

A method of making ethylene glycol is an aspect of the present invention. The method comprises the steps of: i) contacting a reactant capable of producing CO and $H_2$ under hydrothermal conditions at a temperature of at least about 374° C. and a pressure of at least about 22.1 MPa in the presence of water and with an amount of an additive effective to produce a $CO/H_2$ ratio of about 0.66, said contacting being for a time sufficient to produce off-gas having a $CO/H_2$ ratio of about 0.66 and having a $CO/CO_2$ ratio of at least about 0.1; and ii) reacting the off-gas in the presence of a catalyst and at a temperature and a pressure that optimally produces ethylene glycol. The catalyst is typically a transition metal.

A further method of the present invention is a method of producing a carboxylic acid. This method comprises the steps of: i) contacting a reactant capable of producing CO and $H_2$ under hydrothermal conditions at a temperature of at least about 374° C. and a pressure of at least about 22.1 MPa in the presence of water and with an amount of an additive effective to produce a $CO/H_2$ ratio of between about 0.66 and 1.0, said contacting being for a time sufficient to produce off-gas having a $CO/H_2$ ratio of between about 0.66 and 1.0 and having a $CO/CO_2$ ratio of at least about 0.1; and ii) reacting the off-gas in the presence of a catalyst and at a temperature and a pressure that optimally produces the carboxylic acid. Preferred carboxylic acids are acetic, propionic acid, butyric acid or isomers thereof. A more preferred carboxylic acid is acetic acid. In this method, the catalyst is preferably a transition metal or a transition metal oxide.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 symbols are: ○, $CO/CO_2$ @425° C.; □, $CO/H_2$ @425° C.

FIG. 3 symbols are: ○, $CO/CO_2$ @450° C.; □, $CO/H_2$ @450° C.

FIG. 4 symbols are: ○, $CO/CO_2$—$H_3PO_4$; □, $CO/H_2$—$H_3PO_4$; △, $CO/CO_2$—$Na_3PO_4$; ▽, $CO/H_2$—$Na_3PO_4$.

DETAILED DESCRIPTION OF THE PREFERRED EMBODIMENTS

The present invention provides for the use of additives in hydrothermal processing of organic materials to controllably produce particular ratios of $CO/H_2$ in the off-gas.

Figure 1:
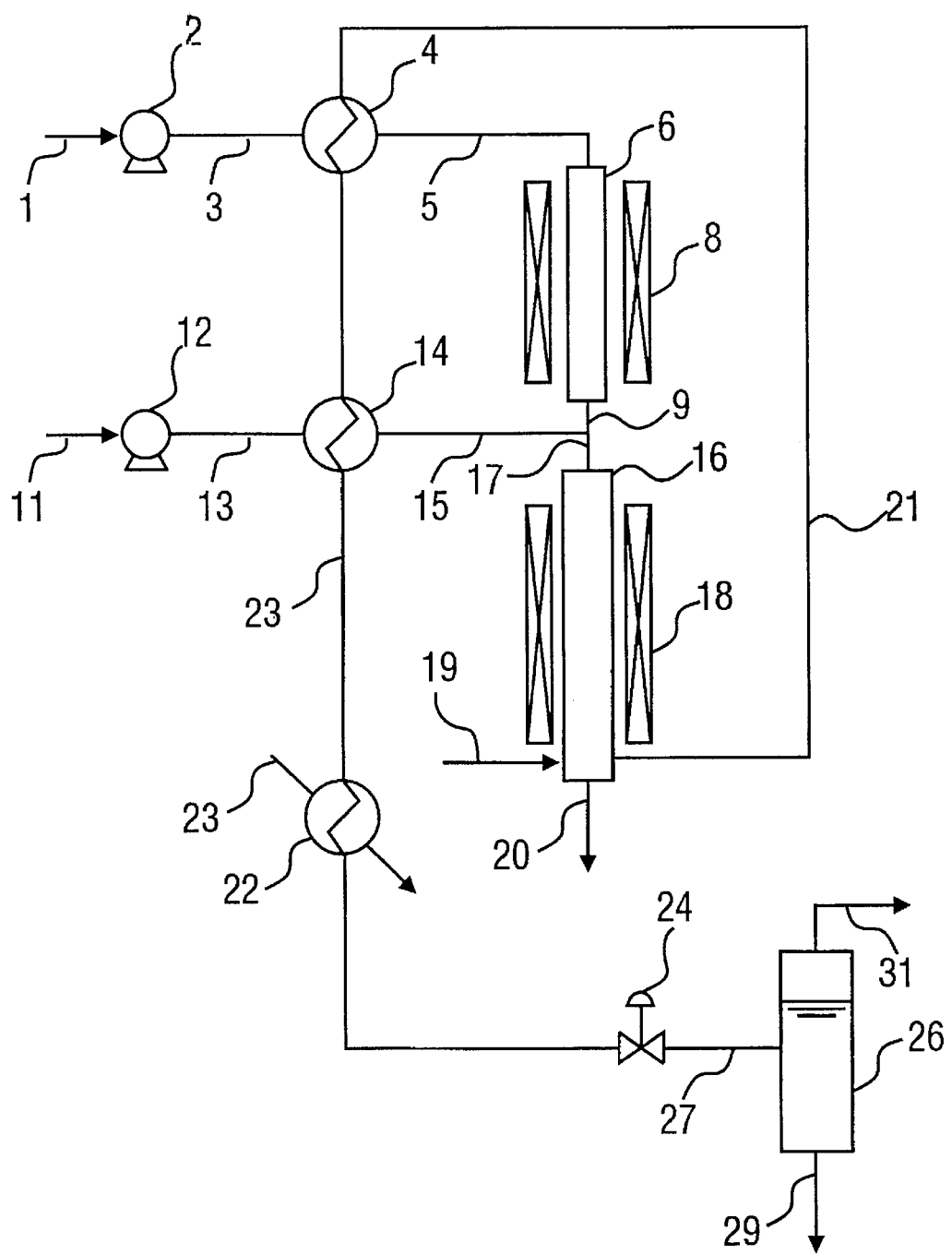
FIG. 1 shows a process flow diagram. The numbers refer to the following: 2,12—feed pumps; 4,14—feed heat exchangers; 6—preheater; 8,18—heaters; 16—reactor; 22—reactor effluent cooler; 24—pressure regulator; 26—gas-liquid separator; 1,11—feed streams; 19—stream containing additives; 20—stream containing precipitated solids; 21—stream containing gaseous products; 25—cooling fluid; 27—low-pressure effluent; 29—liquid product stream; and 31—gas product stream.

FIG. 1 provides a process flow diagram of the reactor used for these studies. The process can be operated via three modes of continuous charge involving two feed lines generating feed streams 1 and 11, and via one mode of continuous charge with a single stream 1. Typically, but not necessarily, the flow rate of a first stream 1 is larger than that of a second stream 11.

Process Mode A: A first aqueous feed 1 containing essentially water is charged into the process via a first pump 2. A second aqueous feed 11 containing an organic compound and an additive is charged into the process via a second pump 12.

Process Mode B: A first aqueous feed 1 containing an organic compound is charged into the process via a first pump 2. A second aqueous feed 11 containing an additive is charged into the process via a second pump 12.

Process Mode C: A first aqueous feed 1 containing an additive is charged into the process via a first pump 2. A second aqueous feed 11 containing an organic compound is charged into the process via a second pump 12.

Process Mode D: The process can also be operated with a single feed line 1 where an aqueous feed containing an organic and an additive is charged into the process via a pump 2.

After the first and second feed streams 1 and 11 are pressurized to near or above the critical pressure for water, they respectively proceed (3 and 13) to heat exchangers 4 and 14. One heat exchanger 14 is optional if direct cold injection of feed stream 11 is preferred. The stream 5 is further heated in a preheater 6 by a heater 8. The temperature of the stream 9 out of the preheater is near or above the critical temperature for water. The temperature of the second stream 15 is below the critical temperature for water. The combined first 9 and second 15 streams form a stream 17 that enters a reactor 16 where additional heating may be provided by a heater 18. Additives may be introduced via line 19 for the purpose of separating $CO_2$ from the reactor effluent. Precipitated solids (such as carbonate salts) are removed through a line 20. Gaseous products are fed to heat exchangers 4 and 14. Exiting from the heat exchangers, a stream 23 can be further cooled by a cooling fluid 25 to a substantially lower temperature before reaching a pressure regulator 24. At lower temperatures and pressures, permanent gases are separated from water in a gas-liquid separator 26. The gas products (off-gas containing the selected ratio of $CO/H_2$) are collected via a line 31 and liquid effluent 29 that may contain refractory compounds may be recycled back to the original feed line 1 or collected to recover liquid products.

The operating procedure generally is as follows. The reactor was first conditioned by heating the first feed stream 1 at a selected flow rate via a first heater 8 and a second heater 18. While the temperature of the reactor was raised, the system pressure was regulated and maintained at a desired test pressure (i.e., above the critical pressure of water) via pressure regulator 24. The temperature at the preheater outlet (stream 9) was controlled near or above the critical temperature of water while the reactor temperature was maintained above the critical temperature of water. After the system pressure and temperature stabilized at the desired values, the second feed stream 11 was introduced. Pumping rates, process stream temperatures, and system pressure were monitored regularly and adjusted, if necessary, to maintain a desired steady-state condition. After the desired steady-state condition had been achieved, liquid effluent 29 and gaseous products 31 were collected over a period of 10–20 min to ensure a good time-averaged representation of the system performance. Instant liquid and gaseous samples (stream 27) were collected in a duration of less than one minute for some studies. Results from the time-averaged and instant samples were generally in good agreement.

Concentrations of DMMP, TDG, and alcohols were measured using a Hewlett Packard (HP Model 5890A) gas chromatograph. Solid-phase extraction cartridges (Supelco LC-Alumina A) were used to remove nonvolatiles from liquid effluent samples to protect the GC columns. Standard concentrations ranged from 1 mg/L to 100 mg/L. The detection limit for most organic species was 1 mg/L.

Concentrations of organic carbon (organic compounds) and inorganic carbon (carbonates) were measured by a Total Organic Carbon Analyzer (Shimadzu Model 5050).

Two gas chromatographs were used for the analysis of gaseous effluents. A Fisher-Hamilton Model 29 gas partitioner, equipped with a silica gel packed column and a thermal conductivity detector, was used to measure carbon dioxide, ethane, ethylene, and hydrogen sulfide. A HP Model 5750 gas chromatograph, equipped with a 5 Å 60/80 molecular sieve packed column and a thermal conductivity detector, was used to analyze carbon monoxide, methane, and hydrogen. Calibration curves were prepared daily. Identification of by-products was accomplished by matching elution times on different GC columns and by spiking samples with the compound of interest and evaluating the response to the spiked sample.

A pH meter (Orion Model SA 720) with a glass electrode (CMS 177-097) was used for pH measurements. The meter was calibrated daily using pH standards. The meter readability was 0.01. Occasionally, pH paper was used as a back up. Readability of the pH paper was 0.2 units.

The conversion of organic compounds into carbon monoxide and hydrogen in supercritical water can be considered as a "reverse Fisher-Tropsch process." The use of additives has two significant impacts on the hydrothermal processing. First, additives can alter the off-gas composition ($CO/H_2$ as well as $CO/CO_2$ ratios). Second, additives can enhance the separation of carbon dioxide from a supercritical water-fluid mixture (such as, CO, $H_2$, $CO_2$, and organic compounds) by forming carbonate salts that, in turn, precipitate from the supercritical water phase.

Several processing scenarios are envisioned to be useful, e.g., the production, in selected amounts and ratios, of (1) $CO+H_2$; (2) $H_2$; (3) CO; (4) $CO_2+H_2$; and (5) $CO_2$. The operating sequences for each processing scenario starts with a readily hydrolyzable or thermally decomposable organic compound in supercritical water and are described below:

The production of $CO+H_2$: A selected $CO/H_2$ ratio in the product stream can be controlled by the presence and amount of an additive. The additive can be alkaline (such as NaOH), acid (such as $H_3PO_4$), a salt (such as $Na_3PO_4$), an oxide (such as $SiO_2$), or an oxidant (such as $H_2O_2$). The present invention demonstrates that the presence of a small amount of additive (1 mol % of the feed carbon) can result in marked changes in the off-gas composition (i.e., $CO/H_2$ ratio). In the case of alkaline additives, metal ions form carbonate and bicarbonate salts with $CO_2$ produced in supercritical water. The solubilities of these carbonate salts in supercritical water are extremely low (<100's mg/L). Therefore, the use of alkaline additives also provides effective separation of $CO_2$ from the off-gas.

The production of $H_2$: The production of $H_2$ may be maximized by increasing the amount of water and reactor residence time to force the water gas-shift reaction to reach equilibrium conditions. If desired, conventional gas separation techniques may be used to separate $H_2$ from the mixture of $CO_2$ and $H_2$.

The production of CO: Typically, higher temperatures and shorter reactor residence times are in favor of CO production. A controlled amount of certain oxidants may be added to consume $H_2$ in the gas mixture. Combustion of hydrogen also produces heat which can be used to maintain the process. Conventional gas separation techniques may be used to separate CO from the mixture of CO and $CO_2$.

The production of $CO_2+H_2$: Similar to the production of $H_2$, a mixture of $CO_2$ and $H_2$ can be obtained from complete CO conversion in SCW. Further gas separation may not be needed.

The production of $CO_2$: Complete oxidation of organic compounds produces $CO_2$, water, and possibly mineral acids. This is the most conventional mode of operation for SCWO processing.

Some organic compounds in a feed stream may be relatively resistant to hydrolysis under supercritical water conditions. In this case, a limited amount of oxidants may be used to break down the starting organic compounds. The intermediates from the oxidative initiation step may undergo hydrolysis or thermal decomposition more easily.

Hydrothermal processing of organic molecules found in wastewaters, sludges, and volatile emissions may be used as a pre-treatment step for synthesis of various compounds. In addition to the use of additives, hydrothermal processing may be operated with limited amounts of oxidant (partial oxidation+hydrolysis+pyrolysis) or without using an oxidant (pyrolysis+hydrolysis).

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Gas Production in Hydrothermal Treatment of Organic Compounds

The present example describes the generation of various gaseous products from hydrothermal treatment of selected organic compounds with or without an oxidant. These results are provided in Table 1 and are highlighted as follows.

In the hydrothermal treatment of dimethyl methylphosphonate (DMMP), methyl phosphonic acid (MPA), methanol, and thiodiglycol (TDG), the yield of carbon monoxide based on organic carbon in the feed was generally much higher than that of carbon dioxide at relatively short reactor residence times. In some cases, greater than 50% of carbon monoxide yields were achieved. Significant amount of hydrogen was produced during TDG hydrolysis with the addition of sodium hydroxide. Generally, distribution of reaction products appear to be affected by processing conditions such as temperature, residence time, and type and amount of oxidant.

Hydrolysis of carboxylic acids, such as, formic, oxalic and tartaric acids, produced large amounts of CO and $H_2$.

TABLE 1

| | | GAS PRODUCTION IN HYDROTHERMAL TREATMENT OF ORGANIC COMPOUNDS | | | | | | | | |
|---|---|---|---|---|---|---|---|---|---|---|
| | | REACTOR | | | | | YIELD* | | | |
| # | FEED | TEMP (°C.) | RT (SEC) | STOICHIOMETRIC (%) | ADDITIVE | FEED CONV. (%) | CO (%) | $CO_2$ (%) | CO/ $CO_2$ | $H_2$ (%) |
| 1 | DMMP | 400 | 18.7 | 105 | $H_2O_2$ | >99 | 19.1 | 4.1 | 4.7 | 0.1 |
| 2 | DMMP | 400 | 18.7 | 125 | $H_2O_2$ | >99 | 12.0 | 1.9 | 6.3 | b/d |
| 3 | DMMP | 400 | 18.7 | 150 | $H_2O_2$ | >99 | 27.6 | 11.3 | 2.4 | b/d |
| 4 | DMMP | 450 | 10.0 | 105 | $H_2O_2$ | >99 | 23.8 | 7.9 | 3.0 | 0.1 |
| 5 | DMMP | 450 | 10.0 | 125 | $H_2O_2$ | >99 | 30.4 | 15.4 | 2.0 | 0.1 |
| 6 | DMMP | 450 | 10.0 | 150 | $H_2O_2$ | >99 | 31.7 | 15.3 | 2.1 | 0.1 |
| 7 | TDG | 400 | 26.0 | 105 | $H_2O_2$ | >99 | 47.4 | 26.1 | 1.8 | 0.1 |

TABLE 1-continued

GAS PRODUCTION IN HYDROTHERMAL TREATMENT OF ORGANIC COMPOUNDS

| | | REACTOR | | | | | YIELD* | | | |
|---|---|---|---|---|---|---|---|---|---|---|
| # | FEED | TEMP (°C.) | RT (SEC) | STOICHIOMETRIC (%) | ADDITIVE | FEED CONV. (%) | CO (%) | $CO_2$ (%) | CO/ $CO_2$ | $H_2$ (%) |
| 8 | TDG | 400 | 26.0 | 125 | $H_2O_2$ | >99 | 26.8 | 30.3 | 0.88 | 0.1 |
| 9 | TDG | 400 | 26.0 | 150 | $H_2O_2$ | >99 | 52.8 | 32.7 | 1.6 | 0.1 |
| 10 | TDG | 450 | 13.9 | 105 | $H_2O_2$ | >99 | 40.4 | 32.5 | 1.2 | 0.7 |
| 11 | TDG | 450 | 13.9 | 125 | $H_2O_2$ | >99 | 38.4 | 32.9 | 1.2 | 0.4 |
| 12 | TDG | 450 | 13.9 | 150 | $H_2O_2$ | >99 | 30.8 | 27.6 | 1.1 | b/d |
| 13 | TDG | 400 | 26.0 | — | NaOH | >99 | b/d | 1.0 | — | 7.1 |
| 14 | TDG | 450 | 13.9 | — | NaOH | >99 | 0.1 | 2.4 | 0.04 | 64.8 |
| 15 | DMMP | 475 | 8.9 | 125 | $O_2$ | >99 | 14.5 | 2.6 | 5.6 | n/r |
| 16 | DMMP | 500 | 8.2 | 125 | $O_2$ | >99 | 13.0 | 6.4 | 2.0 | n/r |
| 17 | DMMP | 525 | 7.6 | 150 | $O_2$ | >99 | 9.5 | 9.6 | 1.0 | n/r |
| 18 | DMMP | 475 | 8.9 | 325 | $O_2$ | >99 | 39.6 | 27.0 | 1.5 | n/r |
| 19 | DMMP | 500 | 8.1 | 325 | $O_2$ | >99 | 16.3 | 37.3 | 0.44 | n/r |
| 20 | DMMP | 525 | 7.6 | 300 | $O_2$ | >99 | 14.5 | 61.2 | 0.24 | n/r |
| 21 | MPA | 500 | 8.2 | 450 | $O_2$ | 30.2 | 19.3 | 13.0 | 1.5 | n/r |
| 22 | MPA | 525 | 7.6 | 325 | $O_2$ | 55.3 | 15.1 | 30.7 | 0.49 | n/r |
| 23 | MeOH | 475 | 8.9 | 275 | $O_2$ | 66.3 | 49.4 | 12.5 | 4.0 | n/r |
| 24 | MeOH | 500 | 8.1 | 175 | $O_2$ | 59.4 | 27.3 | 17.3 | 1.6 | n/r |
| 25 | MeOH | 525 | 7.6 | 200 | $O_2$ | 54.2 | 14.1 | 21.7 | 0.65 | n/r |
| 26 | TDG | 425 | 16.8 | 125 | $O_2$ | 85.9 | 37.4 | 16.3 | 2.3 | n/r |
| 27 | TDG | 425 | 16.8 | 300 | $O_2$ | >99 | 57.1 | 32.0 | 1.8 | n/r |
| 28 | TDG | 450 | 13.9 | 125 | $O_2$ | 92.0 | 48.2 | 28.9 | 1.7 | n/r |
| 29 | TDG | 475 | 12.4 | 125 | $O_2$ | 92.4 | 26.0 | 29.1 | 0.89 | n/r |
| 30 | TDG | 475 | 12.4 | 300 | $O_2$ | >99 | 31.0 | 63.1 | 0.49 | n/r |
| 31 | TDG | 500 | 11.4 | 125 | $O_2$ | 96.0 | 23.8 | 27.5 | 0.87 | n/r |
| 32 | TDG | 525 | 10.6 | 150 | $O_2$ | >99 | 21.6 | 42.5 | 0.51 | n/r |
| 33 | TDG† | 525 | 10.6 | — | None | 72 | 27.6 | n/r | — | n/r |
| 34 | Formic Acid | 475 | n/r | — | None | >99 | 16.1 | 33.2 | 0.48 | n/r |
| 35 | Oxalic Acid | 475 | n/r | — | None | >99 | 32.7 | 30.5 | 1.07 | n/r |
| 36 | Tartaric Acid | 475 | n/r | — | None | >99 | 16.5 | 42.8 | 0.39 | n/r |

Experimental Conditions: Pressure = 27.6 MPa; Feed Concentration = 1000 mg/L;
*yield is based on carbon or hydrogen in the feed (some hydrogen may come from water).
DMMP, dimethyl methylphosphonate; TDG — thiodiglycol.
MeOH, methanol; MPA — methylphosphoric acid.
b/d, below detection limit (0.05% by volume of total off-gas flow).
n/r, not reported.
† also found ethylene (19.3% yield).
Data entries 15–33 are from Turner (1993).
Data entries 34–36 are from Crain (1994).

EXAMPLE 2

EFFECT OF ADDITIVES ON SYN GAS RATIOS

An example is given herein for hydrothermal processing of aqueous feed containing about 1 wt % formic acid. The results summarized in Tables 2 to 4 were averaged values from all samples collected under the same test conditions and are obtained from experiments conducted with process modes A, B, and D, respectively. Carbon closure (carbon recovery) was monitored for each experiment. The rate of carbon input was calculated by multiplying organic carbon concentration (as prepared by gravimetric method and verified by TOC analysis) and the feed flowrate. The rate of carbon output was contributed by 3 carbon species: unreacted organic carbon, CO and $CO_2$. It was assumed that liquid effluents contained unreacted organic carbon and dissolved $CO_2$, which were quantified by TOC and TIC (total inorganic carbon) analyses, respectively. The off-gas composition, containing CO, $CO_2$ and $H_2$, was measured by GC analysis. The carbon closures for these reported experiments were generally within 90%–110%. In the process of producing syn gas from organic materials, the ratio of $CO/CO_2$ indicates the conversion efficiency from organic carbon to CO. Therefore, the following discussion focuses on the molar ratio of $CO/H_2$ and $CO/CO_2$.

The data of Tables 2 and 3 show that the presence of NaOH, $H_3PO_4$ or $NaH_2PO_4$ as an additive increased the amount of feed conversion, increased the yield of CO, decreased the yields of $CO_2$ and $H_2$, and increased the ratios of $CO/CO_2$ and $CO/H_2$. Furthermore, as the amount of additive was increased, i.e., as the additive to feed ratio increased, the above-named changes were greater.

Figure 2:
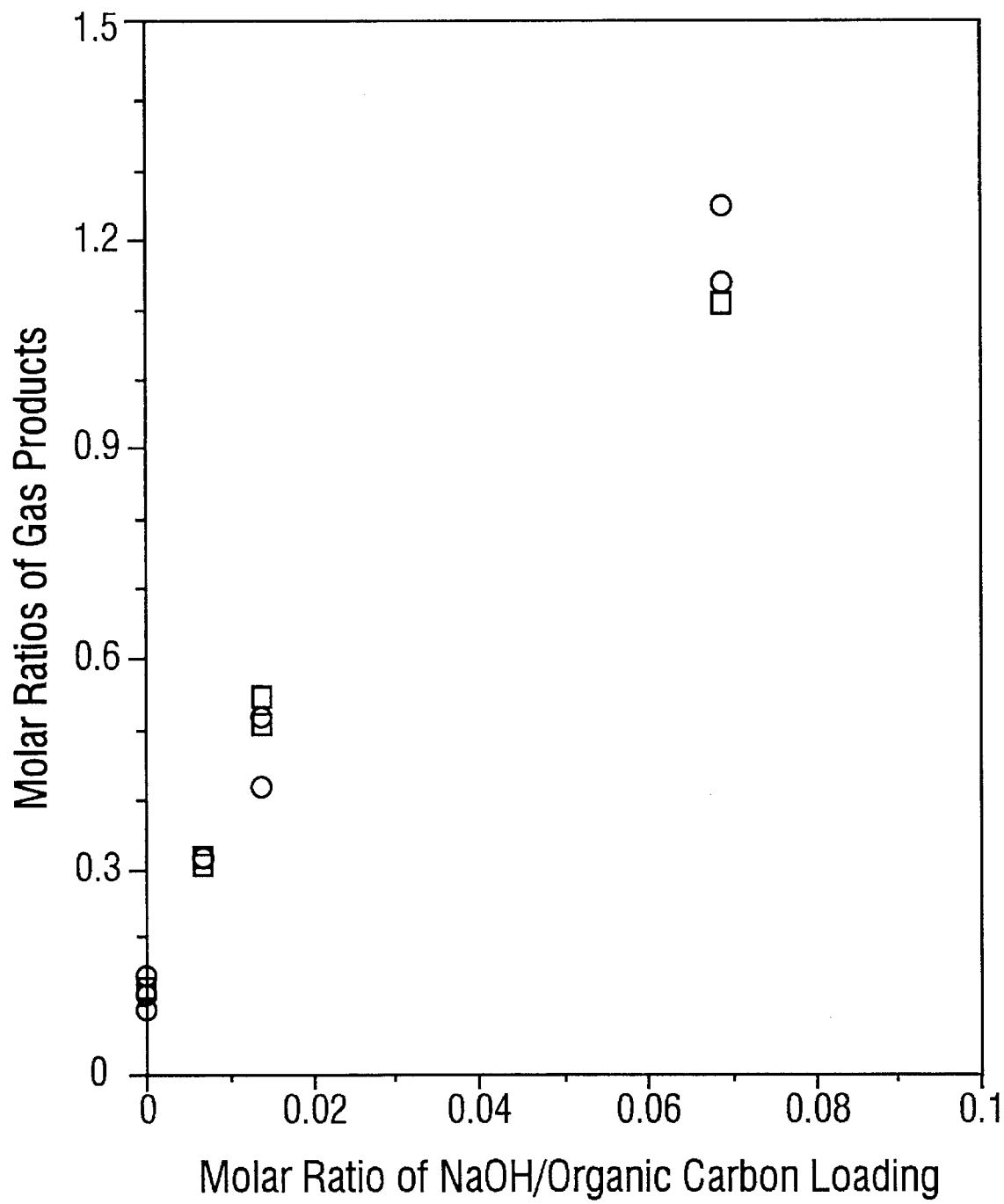
FIG. 2 shows the effect of NaOH on $CO/H_2$ and $CO/CO_2$ ratios at 425° C. Further conditions were: pressure=27.6 MPa; formic acid feed concentration ~1 wt % in water; and reactor residence time=9~14 seconds.
Figure 3:
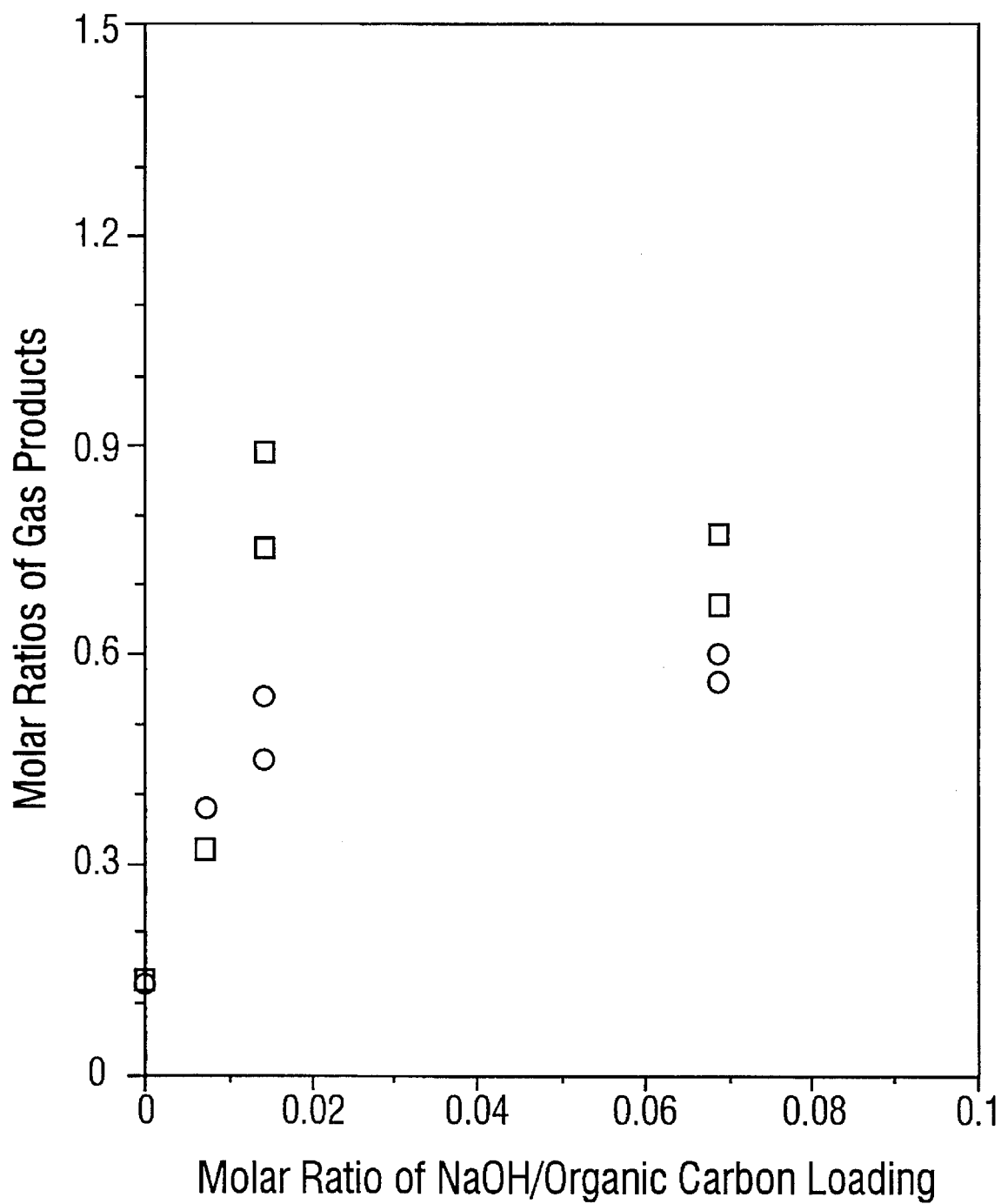
FIG. 3 shows the effect of NaOH on $CO/H_2$ and $CO/CO_2$ ratios at 450° C. Further conditions were as for FIG. 2.
Figure 4:
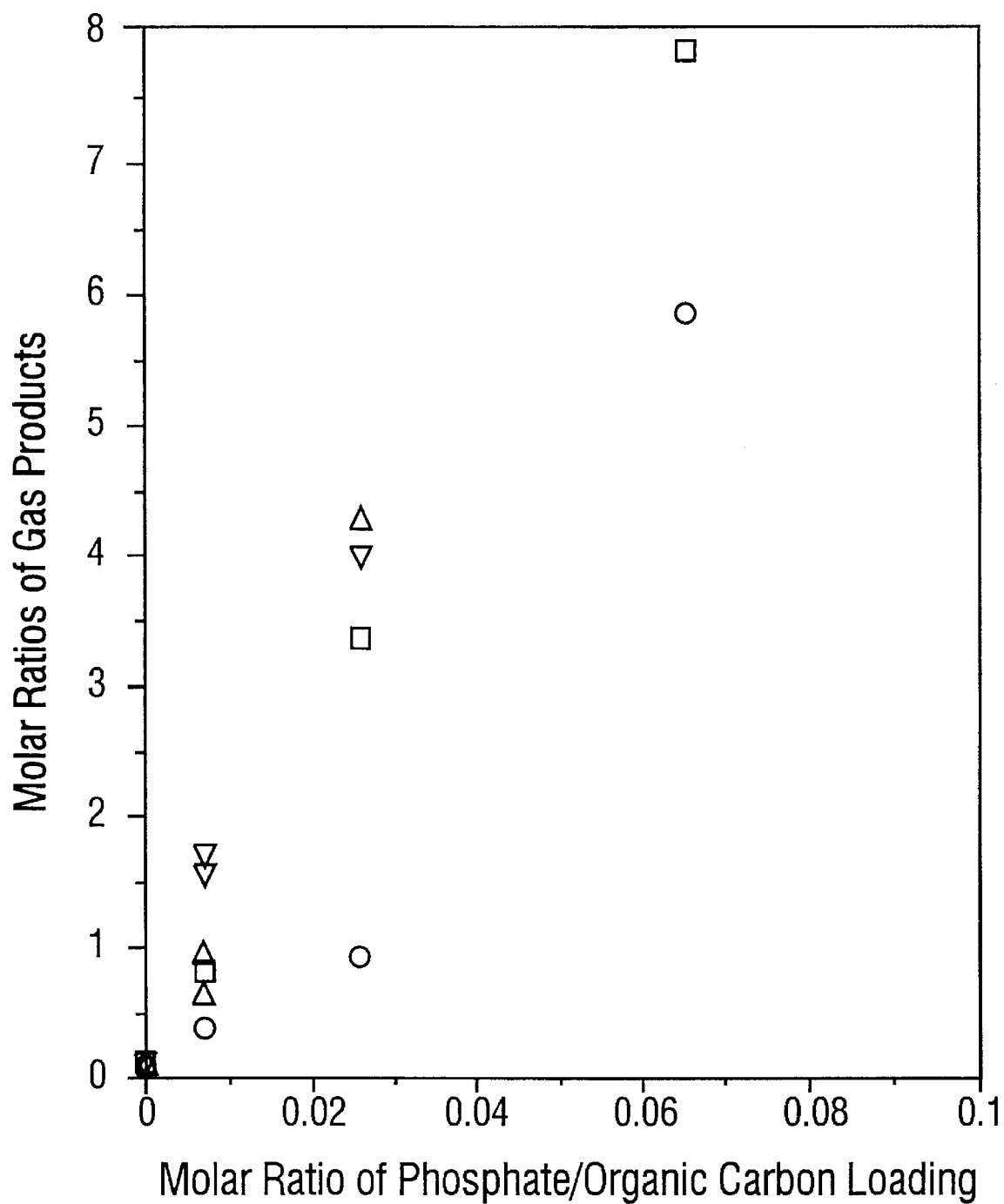
FIG. 4 shows the effect of an acid ($H_3PO_4$) and a salt ($Na_3PO_4$) at 425° C. and additive/organic carbon loading ratios similar to those used in FIG. 2 and FIG. 3. Further conditions were as for FIG. 2.

FIGS. 2 to 4 illustrate the effects of three additives on $CO/H_2$ and $CO/CO_2$ ratios in the product stream of hydrothermal processing formic acid in supercritical water. FIG. 2 shows the effect of sodium hydroxide (NaOH) on $CO/H_2$ and $CO/CO_2$ ratios at 425° C. Without the addition of NaOH, values of about 0.1 were observed for both $CO/H_2$ and $CO/CO_2$ ratios. After adding small amounts of NaOH, ranging from 0.007 to 0.07 molar ratios of NaOH/organic carbon in the feed, both $CO/H_2$ and $CO/CO_2$ ratios showed marked increases (up to about 1.2 for $CO/H_2$ and about 0.9 for $CO/CO_2$). The values accounted for about a ten-fold increase in these ratios. Similarly, FIG. 3 shows the effect of adding NaOH at 450° C. Increases in the $CO/H_2$ and $CO/CO_2$ ratios were also observed. FIG. 4 shows the effect of an acid ($H_3PO_4$) and a salt ($NaH_2PO_4$) at 425° C. and additive/organic carbon loading ratios similar to those used in the NaOH tests. The increases in these ratios were even more dramatic, up to about 80-fold for $CO/H_2$ and 60-fold for $CO/CO_2$.

TABLE 2

GAS PRODUCTION IN HYDROTHERMAL TREATMENT OF ORGANIC COMPOUNDS
(Operated by Process Mode A)

| Organic Compound in Feed | Reactor Temp (°C.) | RT (sec) | Additive | Additive to Feed Ratio | Feed* Conv. (%) | Yield** CO (%) | Yield** $CO_2$ (%) | Yield** $H_2$ (%) | Molar Ratios $CO/CO_2$ | Molar Ratios $CO/H_2$ | Effluent pH |
|---|---|---|---|---|---|---|---|---|---|---|---|
| Formic Acid | 425 | 14 | None | 0 | 64.8 | 8.2 | 91.8 | 72.4 | 0.09 | 0.11 | 2.5 |
| Formic Acid | 425 | 13 | None | 0 | 59.7 | 10.3 | 89.7 | 86.0 | 0.11 | 0.12 | 2.4 |
| Formic Acid | 425 | 13 | None | 0 | 73.7 | 12.2 | 87.8 | 100 | 0.14 | 0.12 | |
| Formic Acid | 425 | 14 | NaOH | 0.007 | 69.7 | 23.8 | 76.2 | 76.8 | 0.31 | 0.31 | 2.5 |
| Formic Acid | 425 | 14 | NaOH | 0.007 | 72.3 | 23.7 | 76.3 | 79.2 | 0.31 | 0.30 | 2.5 |
| Formic Acid | 425 | 14 | NaOH | 0.014 | 85.8 | 33.7 | 66.3 | 62.0 | 0.51 | 0.54 | 2.7 |
| Formic Acid | 425 | 14 | NaOH | 0.014 | 86.0 | 29.1 | 70.9 | 58.0 | 0.41 | 0.50 | 2.7 |
| Formic Acid | 425 | 13 | NaOH | 0.069 | 86.8 | 55.3 | 44.5 | 50.1 | 1.24 | 1.10 | 3.5 |
| Formic Acid | 425 | 13 | NaOH | 0.069 | 84.7 | 52.9 | 47.0 | 48.0 | 1.13 | 1.10 | 3.6 |
| Formic Acid | 450 | 11 | None | 0 | 97.0 | 11.8 | 88.2 | 87.0 | 0.13 | 0.14 | 2.4 |
| Formic Acid | 450 | 11 | NaOH | 0.007 | 96.8 | 27.2 | 72.6 | 86.2 | 0.38 | 0.32 | 3.9 |
| Formic Acid | 450 | 11 | NaOH | 0.014 | 95.4 | 31.0 | 69.0 | 34.7 | 0.45 | 0.89 | 3.0 |
| Formic Acid | 450 | 11 | NaOH | 0.014 | 95.5 | 35.1 | 64.9 | 46.7 | 0.54 | 0.75 | 3.1 |
| Formic Acid | 450 | 11 | NaOH | 0.069 | 95.0 | 35.8 | 64.1 | 46.2 | 0.56 | 0.77 | 3.4 |
| Formic Acid | 450 | 11 | NaOH | 0.069 | 94.7 | 37.4 | 62.5 | 56.2 | 0.60 | 0.67 | 4.0 |
| Formic Acid | 475 | 9 | None | 0 | 98.1 | 12.4 | 87.6 | 82.2 | 0.14 | 0.15 | 3.5 |
| Formic Acid | 475 | 9 | None | 0 | 98.5 | 15.1 | 84.9 | 98.8 | 0.18 | 0.15 | 3.2 |
| Formic Acid | 475 | 9 | NaOH | 0.007 | 96.8 | 26.0 | 74.0 | 101.8 | 0.35 | 0.26 | |
| Formic Acid | 475 | 9 | NaOH | 0.028 | 96.8 | 33.9 | 66.1 | 80.1 | 0.51 | 0.42 | |
| Formic Acid | 425 | 13 | $H_3PO_4$ | 0.007 | 34.4 | 27.5 | 72.5 | 34.1 | 0.38 | 0.81 | 2.5 |
| Formic Acid | 425 | 13 | $H_3PO_4$ | 0.026 | 50.2 | 48.2 | 51.8 | 14.3 | 0.93 | 3.37 | 2.2 |
| Formic Acid | 425 | 13 | $H_3PO_4$ | 0.065 | 56.6 | 85.4 | 14.6 | 10.8 | 5.87 | 7.88 | 2.2 |
| Formic Acid | 425 | 13 | $NaH_2PO_4$ | 0.007 | 39.3 | 39.2 | 60.8 | 25.1 | 0.64 | 1.56 | 2.4 |
| Formic Acid | 425 | 13 | $NaH_2PO_4$ | 0.007 | 35.6 | 49.0 | 51.0 | 28.8 | 0.96 | 1.70 | 2.4 |
| Formic Acid | 425 | 13 | $NaH_2PO_4$ | 0.026 | 92.7 | 81.1 | 18.9 | 20.4 | 4.29 | 3.98 | 3.0 |
| Formic Acid | 425 | 13 | KOH | 0.069 | 88.6 | 37.9 | 61.9 | 71.5 | 0.61 | 0.53 | 4.0 |
| Formic Acid | 425 | 13 | $MnSO_4$ | 0.014 | 65.2 | 15.9 | 84.1 | 62.7 | 0.19 | 0.25 | 2.4 |
| Methanol*** | 475 | 48 | None | 0 | 99.9 | 0 | 100 | 0 | — | — | 4.0 |
| Methanol*** | 475 | 43 | NaOH | 0.014 | 98.6 | 19.8 | 85.5 | 0 | 0.13 | — | 4.0 |
| Methanol*** | 475 | 47 | $H_3PO_4$ | 0.010 | 94.8 | 24.2 | 74.9 | 0 | 0.32 | — | 4.0 |
| Formaldehyde | 425 | 13 | None | 0 | 64.4 | 3.5 | 96.5 | 18.0 | 0.04 | 0.19 | 2.7 |
| Formaldehyde | 425 | 13 | NaOH | 0.006 | 88.2 | 2.7 | 97.3 | 7.0 | 0.03 | 0.39 | 2.8 |
| Formaldehyde | 425 | 13 | NaOH | 0.022 | 76.2 | 2.4 | 97.6 | 10.7 | 0.02 | 0.22 | 3.1 |
| Formaldehyde | 425 | 13 | $H_3PO_4$ | 0.006 | 59.7 | 1.6 | 98.4 | 4.7 | 0.02 | 0.34 | 2.5 |
| Formaldehyde | 425 | 13 | $H_3PO_4$ | 0.022 | 37.6 | 8.1 | 91.9 | 6.7 | 0.09 | 1.20 | 2.3 |
| Formaldehyde | 425 | 13 | $NaH_2PO_4$ | 0.006 | 35.7 | 6.9 | 93.1 | 10.1 | 0.07 | 0.68 | 2.5 |
| Formaldehyde | 425 | 13 | $NaH_2PO_4$ | 0.022 | 36.6 | 7.6 | 92.4 | 6.1 | 0.08 | 1.25 | 2.4 |

Experimental Conditions: Pressure = 27.6 MPa; Feed Concentration ~ 1 wt % organic compound in water.
*Conversion of organic carbon in the feed.
**Yield is based on the carbon or hydrogen contents in the organic feed.
***Hydrogen hydroxide (<100% stoichiometric oxygen demand) was used.

TABLE 3

GAS PRODUCTION IN HYDROTHERMAL TREATMENT OF ORGANIC COMPOUNDS
(Operated by Process Mode B)

| Organic Compound in Feed | Reactor Temp (°C.) | RT (sec) | Additive | Additive to Feed Ratio | Feed* Conv. (%) | Yield** CO (%) | Yield** $CO_2$ (%) | Yield** $H_2$ (%) | Molar Ratios $CO/CO_2$ | Molar Ratios $CO/H_2$ | Effluent pH |
|---|---|---|---|---|---|---|---|---|---|---|---|
| Formic Acid | 425 | 11 | None | 0 | 98.7 | 10.5 | 89.5 | 86.9 | 0.12 | 0.12 | 3.8 |
| Formic Acid | 425 | 11 | $H_3PO_4$ | 0.008 | 70.5 | 25.2 | 74.8 | 78.2 | 0.34 | 0.32 | 2.6 |
| Formic Acid | 425 | 11 | $H_3PO_4$ | 0.08 | 62.6 | 57.7 | 42.3 | 57.4 | 1.36 | 1.00 | 2.2 |
| Formic Acid | 450 | 11 | None | 0 | 98.1 | 12.4 | 87.6 | 94.9 | 0.14 | 0.13 | 3.1 |
| Formic Acid | 450 | 11 | NaOH | 0.007 | 97.7 | 20.8 | 79.2 | 62.3 | 0.26 | 0.33 | 2.3 |
| Formic Acid | 450 | 11 | NaOH | 0.07 | 98.6 | 40.6 | 59.4 | 83.2 | 0.68 | 0.49 | 2.6 |
| Formic Acid | 450 | 11 | $H_3PO_4$ | 0.007 | 83.5 | 31.7 | 68.3 | 77.2 | 0.46 | 0.41 | 2.5 |
| Formic Acid | 450 | 11 | $H_3PO_4$ | 0.07 | 85.3 | 56.6 | 42.5 | 53.0 | 1.30 | 1.07 | 2.2 |
| Formic Acid | 475 | 9 | None | 0 | 99.3 | 14.3 | 85.7 | 99.0 | 0.17 | 0.14 | 4.0 |
| Formic Acid | 475 | 9 | NaOH | 0.009 | 99.2 | 37.6 | 62.4 | 78.2 | 0.60 | 0.48 | 2.2 |
| Formic Acid | 475 | 9 | NaOH | 0.086 | 99.1 | 42.1 | 57.9 | 75.1 | 0.73 | 0.56 | 2.5 |
| Formic Acid | 475 | 9 | $H_3PO_4$ | 0.008 | 98.3 | 30.5 | 69.5 | 82.2 | 0.44 | 0.37 | 4.1 |

TABLE 3-continued

GAS PRODUCTION IN HYDROTHERMAL TREATMENT OF ORGANIC COMPOUNDS
(Operated by Process Mode B)

| Organic Compound in Feed | Reactor Temp (°C.) | RT (sec) | Additive | Additive to Feed Ratio | Feed* Conv. (%) | Yield** CO (%) | CO$_2$ (%) | H$_2$ (%) | Molar Ratios CO/CO$_2$ | CO/H$_2$ | Effluent pH |
|---|---|---|---|---|---|---|---|---|---|---|---|
| Formic Acid | 475 | 9 | H$_3$PO$_4$ | 0.086 | 92.1 | 67.6 | 32.4 | 55.7 | 2.08 | 1.21 | 3.9 |

Experimental Conditions: Pressure = 27.6 MPa; Feed Concentration ~ 1 wt % organic compound in water.
*Conversion of organic carbon in the feed.
**Yield is based on the carbon or hydrogen contents in the organic feed.

TABLE 4

GAS PRODUCTION IN HYDROTHERMAL TREATMENT OF ORGANIC COMPOUNDS
(Operated by Process Mode D)

| Organic Compound in Feed | Reactor Temp (°C.) | RT (sec) | Additive | Additive to Feed Ratio | Feed* Conv. (%) | Yield** CO (%) | CO$_2$ (%) | H$_2$ (%) | Molar Ratios CO/CO$_2$ | CO/H$_2$ | Effluent pH |
|---|---|---|---|---|---|---|---|---|---|---|---|
| Formic Acid | 425 | 14 | None | 0 | 84.9 | 19.3 | 80.7 | 99.3 | 0.24 | 0.19 | 2.9 |
| Formic Acid | 425 | 14 | NaOH | 0.07 | 91.1 | 44.7 | 55.3 | 48.2 | 0.81 | 0.93 | 4.1 |
| Formic Acid | 425 | 14 | NaOH | 0.07 | 90.7 | 46.9 | 53.1 | 47.4 | 0.88 | 0.99 | 4.2 |
| Formate | 425 | 12 | Na$^+$ | 1 | 98.7 | 24.8 | 75.2 | 87.2 | 0.33 | 0.28 | 7.6 |
| Formate | 425 | 12 | Na$^+$ | 1 | 98.9 | 31.0 | 69.0 | 93.0 | 0.45 | 0.33 | 6.2 |
| Formic Acid | 450 | 10 | None | 0 | 92.9 | 23.7 | 76.3 |  | 0.31 | 0.20 | 3.0 |
| Formate | 450 | 10 | Na$^+$ | 1 | 92.7 | 14.4 | 85.6 | 93.5 | 0.17 | 0.15 | 4.6 |
| Formic Acid | 475 | 9 | None | 0 | 100 | 18.4 | 81.6 | 96.6 | 0.23 | 0.19 | 3.2 |

Experimental Conditions: Pressure = 27.6 MPa; Feed Concentration ~ 1 wt % organic compound in water.
*Conversion of organic carbon in the feed.
**Yield is based on the carbon or hydrogen contents in the organic feed.

Results of Table 4 indicate that a small amount of NaOH can increase the CO/H$_2$ and CO/CO$_2$ ratios, however, increasing the amount of additive may not necessarily result in higher ratios. In the case of sodium formate where the ratio of sodium to carbon is one, the CO/H$_2$ and CO/CO$_2$ ratios are lower than those obtained at a Na$^+$/C ratio of 0.07 at 425°, and are lower than control values at 450° C.

Results derived from process modes A, B and D appear to differ, however, no consistent trend appears to exist. The preference of one mode over another is particular to a case. Process mode C is preferred when an oxidant is used as an additive. In this case, the oxidant is pressurized and heated with the feed water. The organic stream is then injected into the hot oxygenated water.

These data demonstrate that the presence of additives affects the amount of carbon present as carbon monoxide and affects the ratio of carbon monoxide to hydrogen obtained during hydrothermal processing.

EXAMPLE 3

EFFECT OF ADDITIVES ON THE WATER-GAS SHIFT REACTION

Formic acid decomposition in supercritical water may occur by the following two global pathways: (1) the formation of CO and H$_2$O and (2) the formation of CO$_2$ and H$_2$. Since CO, H$_2$, CO$_2$, and H$_2$O are present in these hydrothermal reaction mixtures, the water-gas shift (WGS) reaction also has an impact on the off-gas composition. The WGS reaction is:

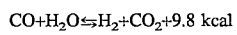

$$CO+H_2O \rightleftharpoons H_2+CO_2+9.8 \text{ kcal}$$

The impact of additives on the observed off-gas composition may have been achieved via altering formic acid decomposition pathways as well as the WGS equilibrium.

The WGS reaction equilibrium is independent of pressure since the reactants are converted into equal numbers of moles of products, and the reaction equilibrium constant (Kp) is a weak function of temperature because the forward reaction (CO conversion) is exothermic with a relatively small heat of reaction. Therefore, pressure and/or temperature adjustments have little effect on the WGS reaction equilibrium composition. However, results from hydrothermal experiments have shown that the use of additives under supercritical water conditions offers possibilities of controlling off-gas composition involving the WGS reaction.

The rate of WGS reaction in supercritical water (at 24.6 MPa and 445° C. to 593° C.) has been reported to be 103.3 exp(–95/RT) [CO]$^{0.71}$ (Holgate et al., 1991). The rate (ln k) for WGS is about –9 (mol/L)$^{0.29}$ s$^{-1}$ at 445° C. and about –6 (mol/L)$^{0.29}$ s$^{-1}$ at 593° C., respectively. At the same pressure and a similar temperature range, the rate (ln k) of direct oxidation of CO by O$_2$ ranges from about –4 (mol/L)$^{-0.30}$ s$^{-1}$ at 420° C. and about 1 (mol/L)$^{-0.30}$ s$^{-1}$ at 570° C. Therefore, at 420° C.–445° C., the rate of WGS reaction is about five-fold slower than that of direct CO oxidation. The existence of commercial WGS processes attributes to the use of various catalysts. Equilibrium gas compositions of the WGS reaction calculated using literature equilibrium constants (ICI, 1970) for the test conditions of interest are given in Tables 5A–5C.

TABLES 5A–5C

Calculated Equilibrium Concentrations for
WGS Reaction Components at 27.6 MPa (4000 psi)
Water-Gas Shift Reaction: $CO + H_2O = CO_2 + H_2$

5A

| | Reactor Condition | | | Feed Composition* | | |
|---|---|---|---|---|---|---|
| # | Temp °C. | Density g/cc | Kp | $[CO]_o$ gmol/L | $[H_2O]_o$ gmol/L | Nt gmol |
| 1 | 400 | 0.2386 | 11.7 | 0.0763 | 13.256 | 13.332 |
| 2 | 425 | 0.1537 | 9.165 | 0.0491 | 8.539 | 8.588 |
| 3 | 450 | 0.1274 | 7.311 | 0.0407 | 7.078 | 7.119 |
| 4 | 475 | 0.1124 | 5.928 | 0.0359 | 6.244 | 6.280 |
| 5 | 500 | 0.1021 | 4.878 | 0.0326 | 5.672 | 5.705 |
| 6 | 525 | 0.0944 | 4.069 | 0.0302 | 5.243 | 5.273 |

5B

Equilibrium Composition at Supercritical State

| # | yCO | $yH_2O$ | $yCO_2$ | $yH_2$ | x |
|---|---|---|---|---|---|
| 1 | 2.8E-06 | 0.9886 | 0.00572 | 0.00572 | 0.9995 |
| 2 | 3.6E-06 | 0.9886 | 0.00572 | 0.00572 | 0.9994 |
| 3 | 4.5E-06 | 0.9886 | 0.00572 | 0.00572 | 0.9992 |
| 4 | 5.5E-16 | 0.9886 | 0.00572 | 0.00572 | 0.9990 |
| 5 | 6.8E-06 | 0.9886 | 0.00571 | 0.00571 | 0.9988 |
| 6 | 8.1E-06 | 0.9886 | 0.00571 | 0.00571 | 0.9986 |

5C

Off-Gas Composition after Removal of Water**

| # | Nt gmol | CO % | $CO_2$ % | $H_2$ % | $CO/CO_2$ | $CO/H_2$ |
|---|---|---|---|---|---|---|
| 1 | 0.1525 | 0.0247 | 49.99 | 49.99 | 0.0005 | 0.0005 |
| 2 | 0.0982 | 0.0315 | 49.98 | 49.98 | 0.0006 | 0.0006 |
| 3 | 0.0814 | 0.0395 | 49.98 | 49.98 | 0.0008 | 0.0008 |
| 4 | 0.0718 | 0.0487 | 49.98 | 49.98 | 0.0010 | 0.0010 |
| 5 | 0.0652 | 0.0592 | 49.97 | 49.97 | 0.0012 | 0.0012 |
| 6 | 0.0603 | 0.0710 | 49.96 | 49.96 | 0.0014 | 0.0014 |

Reference: Equilibrium constants (Kp) were obtained from "Catalyst Handbook", Springer-Verlag New York Inc., ICI Ltd, 1970, (incorporated by reference herein), x = equilibrium conversion (=1 − $[CO]_{eq}/[CO]_o$), y = mole fraction, Nt = total number of moles, $_o$ = initial conditions.
*Assuming that all formic acid in the feed decomposes to CO and $H_2O$. (Formic acid and water concentrations used here are typical of those reported test conditions as described in Tables 2–4).
**Assuming no dissolution of $CO_2$, CO and $H_2$ in water.

The equilibrium ratios $CO/H_2$ (same as $CO/CO_2$) vary from $10^{-4}$ to $10^{-3}$ for the given temperature range. The ratio obtained from the studies of Tables 2–4 indicate that the hydrothermal processing of the present invention did not reach a CO conversion equilibrium, (assuming no additives are present in the system).

Increasing the amount of an additive may not necessarily result in higher ratios of carbon monoxide to hydrogen in the off-gas in hydrothermal processing. In the case of sodium formate of Table 4, where the ratio of sodium to carbon is one, the $CO/H_2$ and $CO/CO_2$ ratios are lower than those obtained at a $Na^+/C$ ratio of 0.07 at 425°, and are lower than control values at 450° C. Additives may enhance the separation of carbon dioxide from a supercritical water-fluid mixture by forming carbonate salts that precipitate from the supercritical water phase. Such precipitation alters the resultant $CO/H_2$ ratio in the gaseous effluent. In this case, the additives are added to a reactor of FIG. 1 after hydrothermal processing at line 19 and the precipitated solids are removed through line 20.

EXAMPLE 4

HYDROTHERMAL PROCESSING AT SUBCRITICAL TEMPERATURES

A variation of the above-described hydrothermal processing method uses Process Mode D and an initial subcritical temperature treatment. In this case, an aqueous feed stream containing an organic compound and an additive is charged into the process at supercritical water pressure and preheater 6 provides heat to substantially convert organic carbon to carbon monoxide at subcritical water temperatures. It is known that substantial amounts of inorganic salts remain dissolved in water at high pressure and subcritical temperature. Therefore, hydrothermal processing at temperatures ranging from about 300° C. to 374° C. will sustain acceptable rates of reactions as well as prevent inorganic salts from massive precipitation. After a selected ratio of $CO/H_2$ is achieved, the resulting mixture enters the reactor 16, the reactor serving as a separator in this case, where the fluid temperature is elevated further to a supercritical state for water via heater 18. Due to the limited solubility of inorganic salts, such as carbonates, in supercritical water, undesired carbon dioxide produced during the subcritical hydrothermal treatment can be substantially precipitated in the form of carbonates. A solids separation device is employed in place of the reactor 16, to remove precipitated salts via line 20, and a relatively $CO_2$-free off-gas is obtained via line 21.

In this case, the additive may be any of those compounds previously described, however, the additive is preferably not an oxidant.

EXAMPLE 5

USE OF SYN GAS AS A FEEDSTOCK

Synthesis gas is a basic feedstock for many chemical processes. For example:
(i) Methanation of synthesis gas is well known. Commercial methanation processes usually involve the use of catalysts (Seglin et al., 1975). The principal reactions associated with methanation are:

$CO\ (gas)+3H_2\ (gas)\rightarrow CH_4\ (gas)+H_2O\ (liquid)$ $CO\ (gas)+H_2O\ (gas)\rightarrow H_2\ (gas)+CO_2\ (gas)$ $CO_2\ (gas)+4H_2\ (gas)\rightarrow CH_4\ (gas)+2H_2O\ (liquid)$ $2CO\ (gas)\rightarrow C\ (solid)+CO_2\ (gas)$ Equilibrium conditions in the methanation system have been studied (Gruber, 1975) and Herman, R. G. (1983) describes the conversion of syn gas to alkanes, and, in particular, methane. Syn gas is reacted in the presence of a catalyst at a temperature and pressure that optimizes the production of methane. A preferred catalyst is cerium-nickel, or a zeolite. Further preferred catalysts include metals such as Y, Nd, Ca, La, Sm, Zr, Pr, Eu, Hf, Th and U.
(ii) Methanol may be produced from syn gas by the following reaction:

$CO+2H_2\rightarrow CH_3OH$

Le Blanc et al. (1994), Chung and Kung (1994) and Herman, R. G. (1983), provide reviews on industrial processes used for the production of methanol. Syn gas is reacted in the presence of a catalyst at a temperature and pressure that optimizes production of methanol. Preferred catalysts are thorium-copper, Cu/ZnO/Cr$_2$O$_3$ or Ca/ZnO/Al$_2$O$_3$.

(iii) The following reactions show that syn gas may form a range of liquid fuel products:

$$nCO + 2nH_2 \rightarrow (CH_2)_n + nH_2O$$

$$2nCO + nH_2 \rightarrow (CH_2)_n + nCO_2$$

This process is known as Fischer-Tropsch Synthesis.

(iv) Syn gas may be used directly as a low or medium—BTU fuel gas.

(v) Formation of acetic acid requires a stoichiometric CO/H$_2$ ratio of 1/1 according to the following reaction.

$$2 \, CO(gas) + 2 \, H_2 \, (gas) \rightarrow CH_3COOH(liquid)$$

The generation of acetic acid directly from synthesis gas, as described in Gustafson and Zoeller, (1993), may be divided into homogeneous Ru-Co system and heterogeneous Rh systems. An example given by Gustafson and Zoeller (1993) stated that when Zr and Li were both added to a Rh-Mn/SiO$_2$ catalyst, the resulting catalyst produced acetic acid at >63% selectivity when operated at 300° C., 100 kg/cm$^2$, and a 9/1 CO/H$_2$ feed ratio. From the processing viewpoint, a significant effect of CO/H$_2$ feed ratio on acetic acid selectivity was noted with high CO/H$_2$ ratios being preferred. The production of acetic acid via methanol carboxylation is also a syn gas-based process. Currently, this process is considered as the method of choice for commercial generation of acetic acid (Zoeller, 1993).

(vi) Ethylene glycol can be obtained from syn gas with a stoichiometric CO/H$_2$ ratio of 2/3 according to the following reaction.

$$2 \, CO(gas) + 3 \, H_2 \, (gas) \rightarrow HOCH_2CH_2OH \, (liquid)$$

The production of ethylene glycol from syn gas is an attractive process since no by-products, such as water, are formed (Suzuki et al., 1984). In a direct reaction, the syn gas is heated in the presence of a catalyst and at a temperature and pressure that optimizes the production of ethylene glycol.

Other uses for syn gas are provided in, for example, Herman, R. G. (1983), Cheng and Kung (1994) and Agreda and Zoeller (1993).

As shown in Table 6, the composition of syn gas, in terms of CO/H$_2$ molar ratio, is also important in specific chemical production applications. An industrially generated syn gas typically has a CO/H$_2$ molar ratio of (1) 1/3 from methane steam reforming; (2) 1/1 from partial oxidation; and (3) 2/1 from coal gasification.

TABLE 6

SYNTHESIS GAS UTILIZATION
IN CHEMICAL PRODUCTION PROCESSES

| CO/H$_2$, Molar Ratio | Chemical Group | Example |
|---|---|---|
| n/(2n + 1) to 2n/(n + 1) | Paraffins | |
| 1/3 | | Methane |
| n/2n to 2n/n | Olefins | |
| 1/2 | | Ethylene |
| n/[(3n + 1)/2] to n/(n + 1) | Alcohols | |
| 1/2 | | Methanol |
| 2/3 | | Ethylene glycol |
| n/[(3n − 2)/2] | Monocarboxylic acids | |
| 1/1 | | Acetic acid |

TABLE 6-continued

SYNTHESIS GAS UTILIZATION
IN CHEMICAL PRODUCTION PROCESSES

| CO/H$_2$, Molar Ratio | Chemical Group | Example |
|---|---|---|
| 2/3 | | Ethyl acetate |
| 4/5 | | Vinyl acetate |
| n/2n to 2n/n | Polymers | | n — the number of carbon atoms.

One skilled in the art, in light of the present specification, would be able to use feedstocks such as ligninocellulosic materials, such as wood, paper, or vegetation; garbage; sewage sludges; fossil fuels; organic wastes from various industrial processes; hydrocarbons; or oxygenated hydrocarbons to produce an off-gas having a selected ratio of CO/H$_2$. A determination of the total carbon content, as described herein, is made on the feedstock in question. A selection of additives and a determination of the amount of additive to add is then made based on the results presented in these Examples and the total carbon content of the feedstock. The same proportion of additive would be selected that was used in the model reactions provided in Tables 2–4. The gaseous effluent would be tested before adding the additive as a control and also after addition of the additive. Of course, some variation in results is expected and one of skill in the art, in light of the present specification, would know how to readily optimize conditions to produce a selected ratio of CO/H$_2$.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agreda, V. H. and J. R. Zoeller, eds., Acetic Acid and its Derivatives, Marcel Dekker, Inc., New York, 1993.

Cheng, W.-H. and Kung, H. H., eds., Methanol Production and Use, Marcel Dekker, Inc., New York, 1994.

Crain, N., "Supercritical Water Oxidation Kinetics of Propellant Simulant," Ph.D. Dissertation, Civil Engineering Department, The University of Texas at Austin, December, 1994.

Gruber, G., "Equilibrium Considerations in the Methane Synthesis System," in *Methanation of Synthesis Gas*, edited by L. Seglin, Advances in Chemistry Series 146, American Chemical Society, Washington, D.C., 1975.

Gustafson, B. L. and Zoeller, J. R. "Other Synthesis Gas-Based Acetic Acid Processes," in Acetic Acid and its Derivatives, edited by V. H. Agreda and J. R. Zoeller, Marcel Dekker, Inc., New York, 1993.

Herman, R. G., ed. *Catalytic Conversions of Synthesis Gas and Alcohols to Chemicals*, Plenum Press, New York, 1984.
Holgate, H. R., et al. Presented at the AIChE Annual Meeting, Nov. 17–22, 1991, Los Angeles, Calif.
ICI Ltd., Catalyst Handbook, 1970.
LeBlanc, J. R. et al. "Production of Methanol," in *Methanol Production and Use*, edited by Cheng, W.-H. and Kung, H. H., Marcel Dekker, Inc., New York, 1994.
Seglin, L. et al., "Survey of Methanation Chemistry and Processes," in *Methanation of Synthesis Gas* edited by L. Seglin, Advances in Chemistry Series 146, American Chemical Society, Washington, D.C., 1975.
Suzuki, S. et al. "Ethylene Glycol from Methanol and Synthesis Gas via Glycolic Acid," in *Catalytic Conversions of Synthesis Gas and Alcohols to Chemicals*, edited by R. G. Herman, Plenum Press, New York, 1984.
Turner, M. D. Ph.D. Dissertation, Civil Engineering Department, The University of Texas at Austin, Austin, Tex., December 1993.
Zoeller, J. R. "Manufacture via Methanol Carboxylation," in Acetic Acid and its Derivatives, edited by V. H. Agreda and J. R. Zoeller, Marcel Dekker, Inc., New York, 1993.
U.S. Pat. No. 3,716,474 (Feb. 13, 1973).
U.S. Pat. No. 4,251,227 (Feb. 17, 1981).
U.S. Pat. No. 4,465,888 (Aug. 14, 1984).
U.S. Pat. No. 4,483,761 (Nov. 20, 1984).
U.S. Pat. No. 4,594,141 (Jun. 10, 1986).
U.S. Pat. No. 4,840,725 (Jun. 20, 1989).
U.S. Pat. No. 5,133,877 (Jul. 28, 1992).
U. S. Pat. 5,232,604 (Aug. 3, 1993).
U.S. Pat. No. 5,250,193 (Oct. 5, 1993).
JP 5031000 (Feb. 9, 1993).
AU 82/85597.
BR 8204075 (Jan. 27, 1983).

What is claimed is:

1. A method of producing an off-gas with a selected $CO/H_2$ ratio of from about 0.1 to about 8 and a $CO/CO_2$ ratio of at least about 0.1 by hydrothermal processing of a reactant capable of producing CO and $H_2$ under hydrothermal conditions, the method comprising:

contacting the reactant at a temperature of at least about 374° C. and a pressure of at least about 22.1 MPa in the presence of water and with an amount of an additive effective to produce the selected $CO/H_2$ ratio, said contacting being for a time sufficient to produce off-gas having the selected $CO/H_2$ ratio and having a $CO/CO_2$ ratio of at least about 0.1;

wherein the reactant capable of producing CO and $H_2$ under hydrothermal conditions is selected from the group consisting of hydrocarbons, oxygenated hydrocarbons, organic wastes, lignocellulosic materials, sewage sludge, industrial sludge, and fossil fuels;

and wherein the additive effective to produce the selective $CO/H_2$ ratio is selected from the group consisting of acids, bases, salts, oxides, or oxidants.

2. The method of claim 1 further comprising preheating the reactant before the contacting step.

3. The method of claim 1 wherein the reactant capable of producing CO and $H_2$ under hydrothermal conditions comprises a hydrocarbon, an oxygenated hydrocarbon, a phosphonate, an organic acid, an alkyl phosphonic acid, an alcohol, a glycol, or an aldehyde.

4. The method of claim 1 wherein the additive effective to produce the selected $CO/H_2$ ratio is an organic or inorganic acid; a hydroxide base of a Group IA, Group IIA or transition metal; a salt of a Group IA, Group IIA or transition metal and an organic or inorganic acid; an oxide of a group IIIA element, a Group IVA element or a peroxide; or oxygen or hydrogen peroxide.

5. The method of claim 1 wherein the additive is an acid, and the acid is selected from the group consisting of boric, carbonic, hydrogen halide, nitric, phosphoric, and sulfuric acid.

6. The method of claim 1 wherein the additive is a base, and the base is a hydroxide form of a group IA metal, group IIA metal, or a transition metal.

7. The method of claim 1 wherein the additive is a salt.

8. The method of claim 1 wherein the additive is an oxide, and the oxide is an oxide of a group IIIA element, an oxide of a group IVA element, or a peroxide.

9. The method of claim 1 wherein the additive is an oxidant.

10. The method of claim 9 wherein the oxidant is oxygen or hydrogen peroxide.

11. The method of claim 1 wherein the time is between about 5 and 300 seconds.

12. The method of claim 1 wherein the time is between about 5 and 100 seconds.

13. The method of claim 1 wherein the time is between about 7 and 14 seconds.

14. The method of claim 1 where the acid is phosphoric acid.

15. The method of claim 1 where the base is NaOH.

16. The method of claim 1 where the additive is added in an amount less than or equal to the solubility of the additive during the contacting step.

17. The method of claim 1 where the additive is added in an amount sufficient to precipitate $CO_2$.

18. The method of claim 1 where the additive is added in a molar ratio to carbon in the reactant of between about 0.001 and 0.1.

19. The method of claim 1 where the additive is added in a molar ratio to carbon in the reactant of about 1.0.

20. The method of claim 1 where the temperature is between about 400° C. and 500° C.

21. The method of claim 1 further comprising the step of obtaining the off-gas with a selected $CO/H_2$ ratio.

22. The method of claim 21 further comprising the step of using the off-gas for synthesis of organic compounds.

23. The method of claim 22 where the off-gas has a selected $CO/H_2$ ration of about 0.33 and is used for the synthesis of alkanes.

24. The method of claim 22 wherein the off-gas has a selected $CO/H_2$ ratio of about 0.5 and is used for the synthesis of alkenes.

25. The method of claim 22 where the off-gas has a selected $CO/H_2$ ratio of between about 0.5 and 0.66 and is used for the synthesis of alcohols.

26. The method of claim 22 where the off-gas has a selected $CO/H_2$ ratio of between about 0.66 and 1.0 and is used for the synthesis of carboxylic acids or esters.

27. A method of producing an alkane comprising the steps of:

contacting a reactant capable of producing CO and $H_2$ under hydrothermal conditions at a temperature of at least about 374° C. and a pressure of at least about 22.1 MPa in the presence of water and with an amount of an additive effective to produce a $CO/H_2$ ratio of about 0.33, said contacting being for a time sufficient to produce off-gas having a $CO/H_2$ ratio of about 0.33 and having a $CO/CO_2$ ratio of at least about 0.1; and reacting the off-gas in the presence of a catalyst and at a temperature and a pressure that optimally produces the alkane;

wherein the reactant capable of producing CO and $H_2$ under hydrothermal conditions is selected from the group consisting of hydrocarbons; oxygenated hydrocarbons; organic wastes, lignocellulosic materials, sewage sludge; industrial sludge or fossil fuels;

and wherein the additive effective to produce the selective $CO/H_2$ ratio is selected from the group consisting of acids, bases, salts, oxides, or oxidants.

28. The method of claim 27 where the alkane is methane.

29. The method of claim 27 where the catalyst is cerium-nickel or a zeolite.

30. The method of claim 27 where the catalyst is a metal selected from the group consisting of Y, La, Pr, Th, Nd, Sm, Eu, U, Ca, Zr, and Hf.

31. A method of producing an alcohol comprising the steps of:

contacting a reactant capable of producing CO and $H_2$ under hydrothermal conditions at a temperature of at least about 374° C. and a pressure of at least about 22.1 MPa in the presence of water and with an amount of an additive effective to produce a $CO/H_2$ ratio of between about 0.5 and 0.66, said contacting being for a time sufficient to produce off-gas having a $CO/H_2$ ratio of between about 0.5 and 0.66 and having a $CO/CO_2$ ratio of at least about 0.1; and reacting the off-gas in the presence of a catalyst and at a temperature and a pressure that optimally produces the alcohol;

wherein the reactant capable of producing CO and $H_2$ under hydrothermal conditions is selected from the group consisting of hydrocarbons; oxygenated hydrocarbons; organic wastes, lignocellulosic materials, sewage sludge; industrial sludge or fossil fuels;

and wherein the additive effective to produce the selective $CO/H_2$ ratio is selected from the group consisting of acids, bases, salts, oxides, or oxidants.

32. The method of claim 31 where the alcohol is methanol.

33. The method of claim 31 where the catalyst is thorium-copper, $Cu/ZnO/Cr_2O_3$ or $Cu/ZnO/Al_2O_3$.

34. A method of producing ethylene glycol comprising the steps of:

contacting a reactant capable of producing CO and $H_2$ under hydrothermal conditions at a temperature of at least about 374° C. and a pressure of at least about 22.1 MPa in the presence of water and with an amount of an additive effective to produce a $CO/H_2$ ratio of about 0.66, said contacting being for a time sufficient to produce off-gas having a $CO/H_2$ ratio of about 0.66 and having a $CO/CO_2$ ratio of at least about 0.1; and reacting the off-gas in the presence of a catalyst and at a temperature and a pressure that optimally produces ethylene glycol;

wherein the reactant capable of producing CO and $H_2$ under hydrothermal conditions is selected from the group consisting of hydrocarbons; oxygenated hydrocarbons; organic wastes, lignocelulosic materials sewage sludge; industrial sludge or fossil fuels;

and wherein the additive effective to produce the selective $CO/H_2$ ratio is selected from the group consisting of acids, bases, salts, oxides, or oxidants.

35. The method of claim 34 where the catalyst is a transition metal.

36. A method of producing a carboxylic acid comprising the steps of:

contacting a reactant capable of producing CO and $H_2$ under hydrothermal conditions at a temperature of at least about 374° C. and a pressure of at least about 22.1 MPa in the presence of water and with an amount of an additive effective to produce a $CO/H_2$ ratio of between about 0.66 and 1.0, said contacting being for a time sufficient to produce off-gas having a $CO/H_2$ ratio of between about 0.66 and 1.0 and having a $CO/CO_2$ ratio of at least about 0.1; and reacting the off-gas in the presence of a catalyst and at a temperature and a pressure that optimally produces the carboxylic acid;

wherein the reactant capable of producing CO and $H_2$ under hydrothermal conditions is selected from the group consisting of hydrocarbons; oxygenated hydrocarbons; organic wastes, lignocellulosic materials, sewage sludge; industrial sludge or fossil fuels;

and wherein the additive effective to produce the selective $CO/H_2$ ratio is selected from the group consisting of acids, bases, salts, oxides, or oxidants.

37. The method of claim 36 where the carboxylic acid is acetic acid.

38. The method of claim 36 where the catalyst is a transition metal or a transition metal oxide.

39. A method of producing an off-gas with a selected $CO/H_2$ ratio of from about 0.1 to about 8 by hydrothermal processing of a reactant capable of producing CO and $H_2$ under hydrothermal conditions, the method comprising:

contacting the reactant at a temperature of between about 300° C. and 374° C. and a pressure of at least about 22.1 MPa in the presence of water and with an amount of an additive effective to produce the selected $CO/H_2$ ratio, said contacting being for a time sufficient to produce off-gas having the selected $CO/H_2$ ratio; and heating the mixture to at least about 374° C. to remove carbon dioxide as a carbonate salt to produce off-gas having a $CO/CO_2$ ratio of at least about 0.1;

wherein the reactant capable of producing CO and $H_2$ under hydrothermal conditions is selected from the group consisting of hydrocarbons; oxygenated hydrocarbons; organic wastes, lignocellulosic materials. sewage sludge; industrial sludge or fossil fuels;

and wherein the additive effective to produce the selective $CO/H_2$ ratio is selected from the group consisting of acids, bases, salts, oxides, or oxidants.

40. The method of claim 1 or 3 wherein the selected $CO/H_2$ ratio is from about 0.2 to 4.0.

41. The method of claim 1 or 3 wherein the selected $CO/H_2$ ratio is from about 0.3 to 2.0.

42. The method of claim 1 or 3 wherein the selected $CO/H_2$ ratio is from about 0.3 to 1.5.

43. The method of claim 1 or 3 wherein the $CO/CO_2$ ratio is at least about 0.2.

44. The method of claim 27, 31, 34, or 36 wherein the additive is an acid, and the acid is selected from the group consisting of boric, carbonic, hydrogen halide, nitric, phosphoric, and sulfuric acid.

45. The method of claim 27, 31, 34, or 36 wherein the additive is a base, and the base is a hydroxide form of a group IA metal, group IIA metal, or a transition metal.

46. The method of claim 27, 31, 34, or 36 wherein the additive is a salt.

47. The method of claim 27, 31, 34, or 36 wherein the additive is an oxide, and the oxide is an oxide of a group IIIA element, a group IVA element, or a peroxide.

48. The method of claim 27, 31, 34, or 36 wherein the additive is an oxidant.

49. The method of claim 48 wherein the oxidant is oxygen or hydrogen peroxide.

* * * * *

UNITED STATES PATENT AND TRADEMARK OFFICE
CERTIFICATE OF CORRECTION

PATENT NO. : 5,578,647
DATED : November 26, 1996
INVENTOR(S) : Li et al.

It is certified that error appears in the above-identified patent and that said Letters Patent is hereby corrected as shown below:

In claim 23, column 20, line 44, delete "ration" and insert --ratio-- therefor.

In claim 24, column 20, line 46, delete "wherein" and insert --where-- therefor.

Signed and Sealed this

First Day of April, 1997

Attest:

BRUCE LEHMAN

Attesting Officer

Commissioner of Patents and Trademarks